(12) United States Patent
Yilmaz

(10) Patent No.: US 11,191,911 B2
(45) Date of Patent: Dec. 7, 2021

(54) RECEPTACLE, CARTRIDGE, APPARATUS AND METHODS FOR GENERATING AN INHALABLE MEDIUM

(71) Applicant: BRITISH AMERICAN TOBACCO (INVESTMENTS) LIMITED, London (GB)

(72) Inventor: Ugurhan Yilmaz, London (GB)

(73) Assignee: BRITISH AMERICAN TOBACCO (INVESTMENTS) LIMITED, London (GB)

( * ) Notice: Subject to any disclaimer, the term of this patent is extended or adjusted under 35 U.S.C. 154(b) by 177 days.

(21) Appl. No.: 16/322,242

(22) PCT Filed: Aug. 8, 2017

(86) PCT No.: PCT/EP2017/070049
§ 371 (c)(1),
(2) Date: Jan. 31, 2019

(87) PCT Pub. No.: WO2018/029186
PCT Pub. Date: Feb. 15, 2018

(65) Prior Publication Data
US 2019/0166919 A1 Jun. 6, 2019

(30) Foreign Application Priority Data
Aug. 9, 2016 (GB) ...................................... 1613688

(51) Int. Cl.
*H01R 13/62* (2006.01)
*A61M 15/06* (2006.01)
(Continued)

(52) U.S. Cl.
CPC ............. *A61M 15/06* (2013.01); *A24F 40/30* (2020.01); *A24F 40/42* (2020.01); *A24F 40/485* (2020.01);
(Continued)

(58) Field of Classification Search
CPC ... A24F 47/008; A61M 11/042; A61M 15/06; A61M 2016/0024; A61M 2205/3653
(Continued)

(56) References Cited

U.S. PATENT DOCUMENTS 5,105,831 A  4/1992 Banerjee et al.
5,865,186 A  2/1999 Volsey, II
(Continued)

FOREIGN PATENT DOCUMENTS

CL  2012003238 A1  5/2013
CL  2012003240 A1  5/2013
(Continued)

OTHER PUBLICATIONS

International Search Report and Written Opinion, Application No. PCT/EP2017/070049, dated Dec. 1, 2017, 13 pages.
(Continued)

*Primary Examiner* — Khiem M Nguyen
(74) *Attorney, Agent, or Firm* — Patterson Thuente Pedersen, P.A.

(57) ABSTRACT

There is provided a receptacle for use with an apparatus for generating an inhalable medium, the receptacle including a chamber for containing a flavor material, whereby, in use, at least one of a vapor and an aerosol generated by the apparatus can flow through the flavor material to entrain one or more constituents from the flavor material to produce the inhalable medium. The receptacle is configured to maintain an air gap separation between an outlet end of the chamber and flavor material when it is received in the chamber, the outlet end being configured to enable the inhalable medium to flow out of the chamber.

31 Claims, 6 Drawing Sheets

(51) Int. Cl.
  *A61M 11/04*  (2006.01)
  *A24F 40/30*  (2020.01)
  *A24F 40/42*  (2020.01)
  *A24F 40/485* (2020.01)
  *A61M 16/00*  (2006.01)
  *A24F 40/10*  (2020.01)
  *A24F 40/20*  (2020.01)

(52) U.S. Cl.
  CPC ............ *A61M 11/042* (2014.02); *A24F 40/10* (2020.01); *A24F 40/20* (2020.01); *A61M 2016/0024* (2013.01); *A61M 2205/3653* (2013.01); *A61M 2205/8206* (2013.01)

(58) Field of Classification Search
  USPC .................................................. 131/329, 330
  See application file for complete search history.

(56) References Cited

U.S. PATENT DOCUMENTS

| | | | |
|---|---|---|---|
| 8,991,402 B2* | 3/2015 | Bowen ................ | A61M 11/047 131/194 |
| D782,728 S | 3/2017 | Pinder | |
| D805,684 S | 12/2017 | Thuery | |
| D815,342 S | 4/2018 | Sutton | |
| 10,842,954 B2* | 11/2020 | Reevell ................. | A24F 40/42 |
| 2008/0092912 A1 | 4/2008 | Robinson | |
| 2009/0151717 A1* | 6/2009 | Bowen ................ | A61M 11/048 128/200.23 |
| 2011/0226236 A1 | 9/2011 | Buchberger | |
| 2013/0192615 A1 | 8/2013 | Tucker et al. | |
| 2015/0374035 A1 | 12/2015 | Sanchez et al. | |
| 2016/0073695 A1 | 3/2016 | Sears et al. | |

FOREIGN PATENT DOCUMENTS

| | | |
|---|---|---|
| EP | 0336458 A2 | 10/1989 |
| EP | 2989912 | 3/2016 |
| GB | 2511303 A | 9/2014 |
| GB | 2529201 | 2/2016 |
| JP | 2015512617 A | 4/2015 |
| JP | 2015513922 A | 5/2015 |
| WO | WO-2015179388 A1 | 11/2015 |
| WO | WO-2016024083 A1 | 2/2016 |
| WO | WO-2016062777 A1 | 4/2016 |
| WO | WO 2017055584 | 4/2017 |

OTHER PUBLICATIONS

International Preliminary Report on Patentability for Application No. PCT/EP2017/070049, dated Feb. 21, 2019, 9 pages.
Office Action dated Apr. 1, 2020 for Canadian Application No. 3033324, 6 pages.
Office Action dated May 19, 2020 for Japanese Application No. 2019-505139, 4 pages.
Office Action dated Mar. 2, 2020 for Chilean Application No. 201900320, 14 pages.
European Communication for EP Application 17761018.5 dated May 26, 2021.
Korean Notification for KR10-2019-7003865 dated May 25, 2021.

* cited by examiner

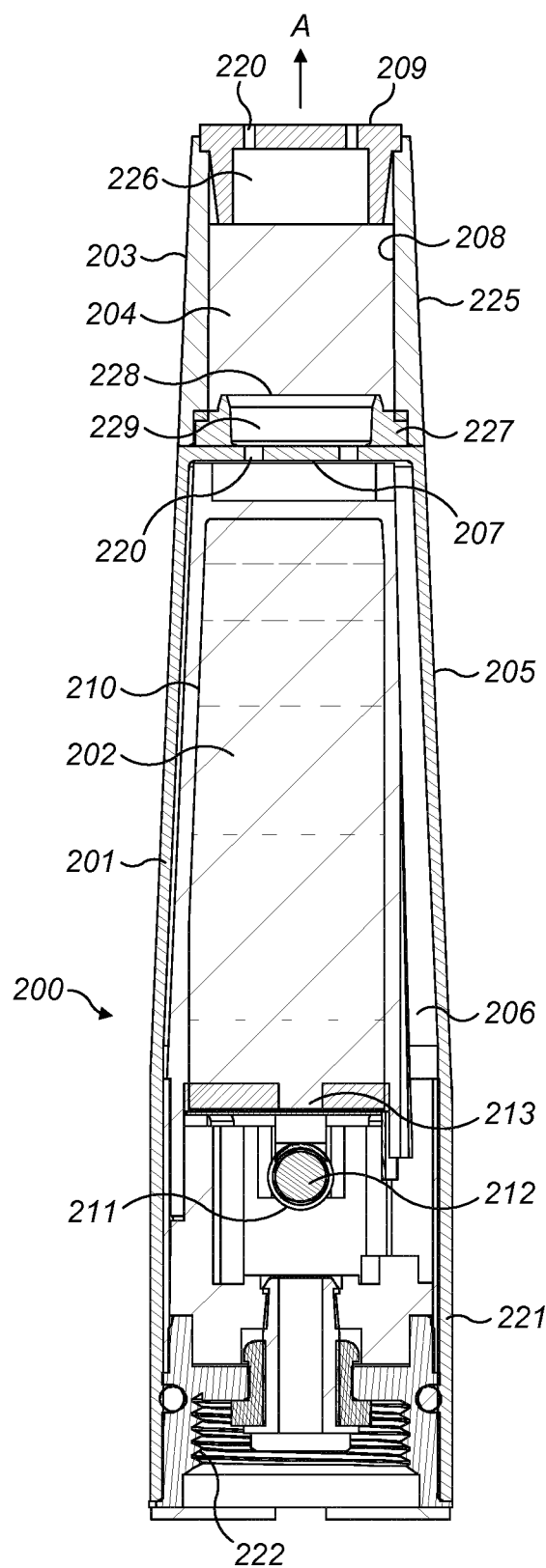
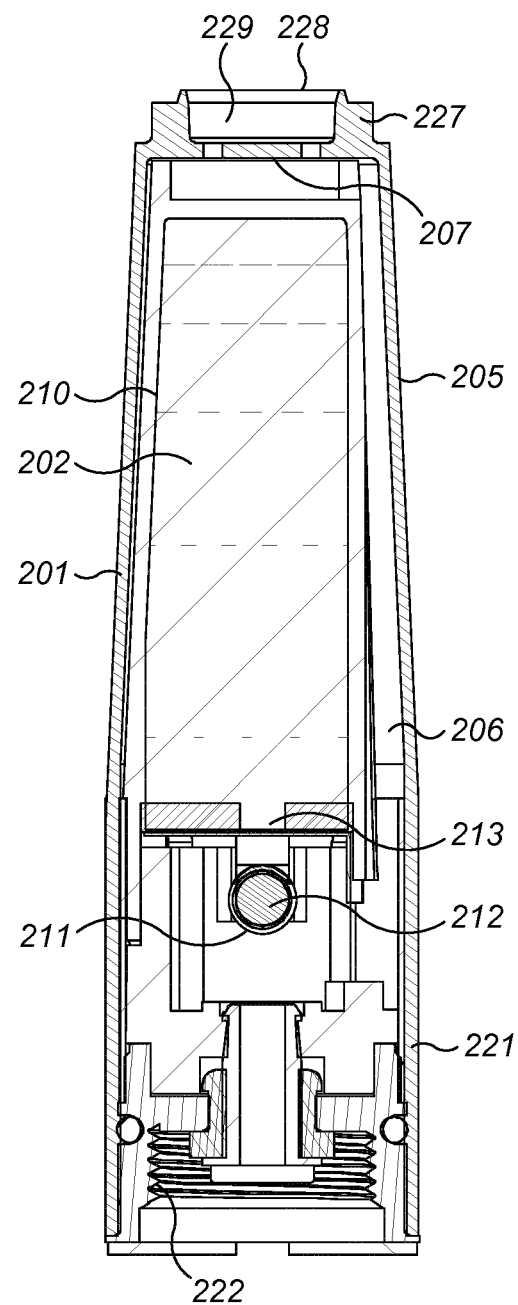
FIG. 3a
FIG. 3b

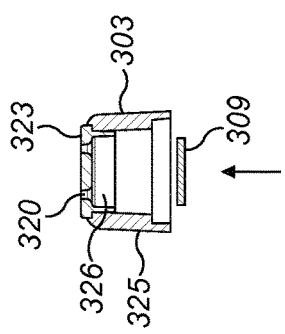
FIG. 4e
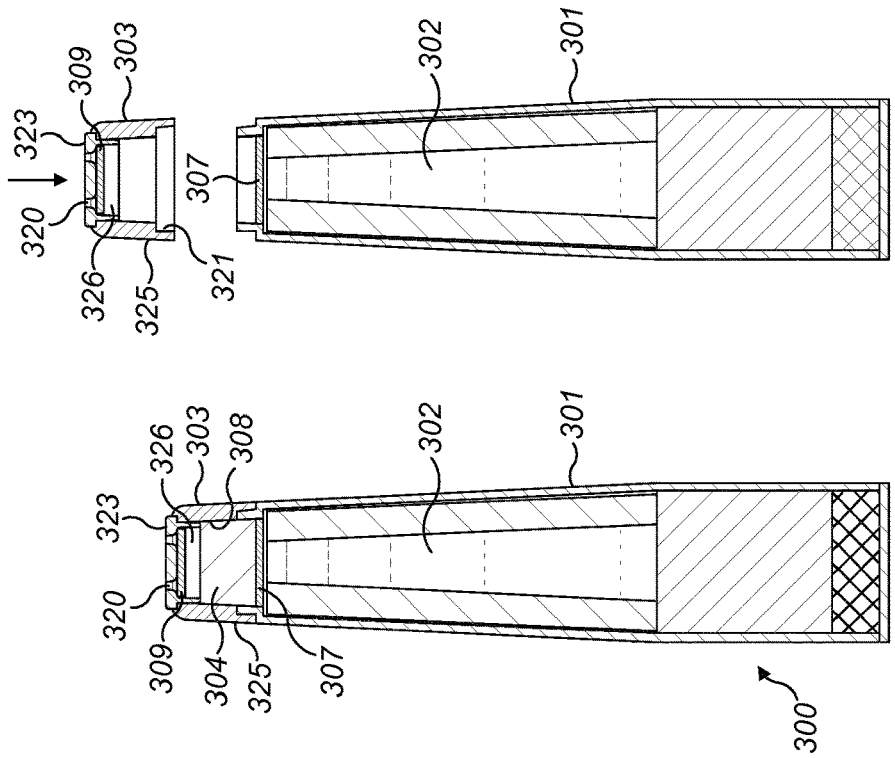
FIG. 4d
FIG. 4c
FIG. 4b
FIG. 4a

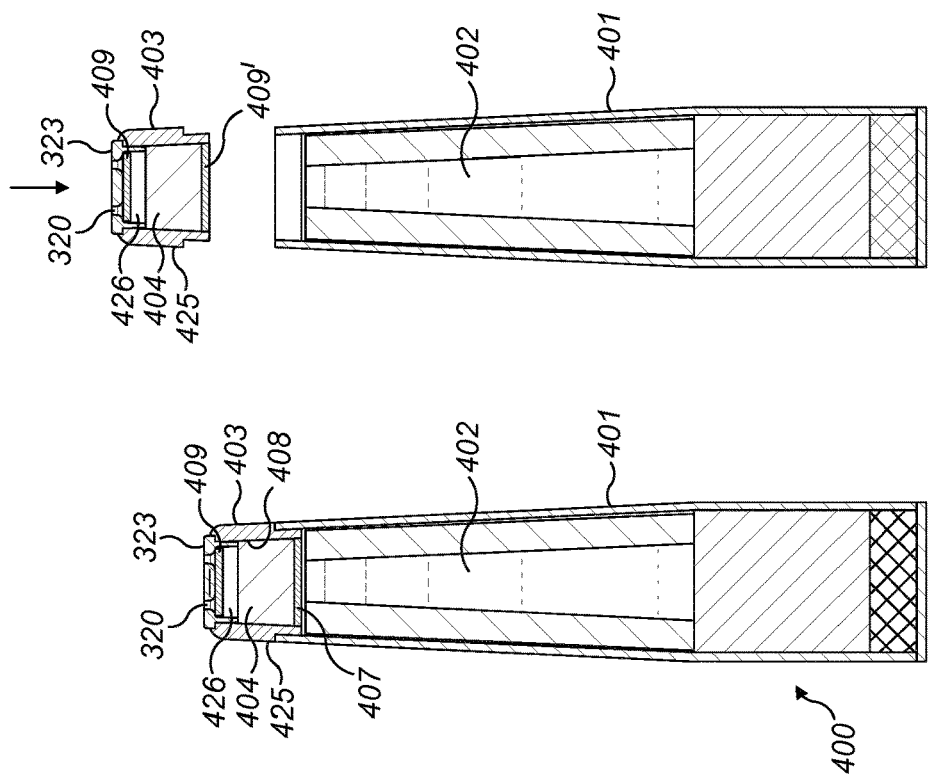
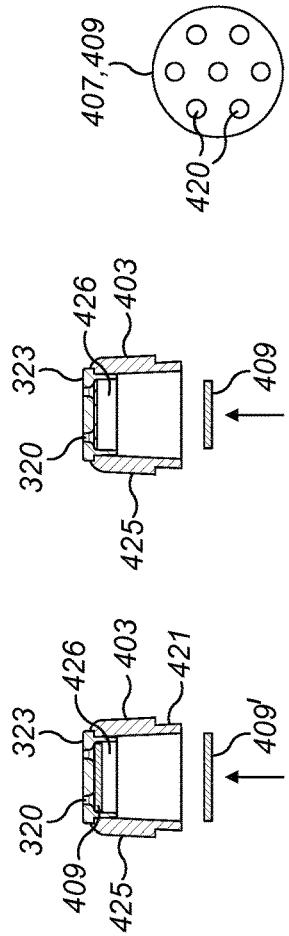
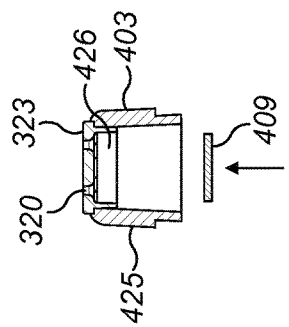
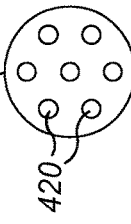

RECEPTACLE, CARTRIDGE, APPARATUS AND METHODS FOR GENERATING AN INHALABLE MEDIUM

PRIORITY CLAIM

The present application is a National Phase entry of PCT Application No. PCT/EP2017/070049, filed Aug. 8, 2017, which claims priority from GB Patent Application No. 1613688.9, filed Aug. 9, 2016, which is hereby fully incorporated herein by reference.

TECHNICAL FIELD

The present disclosure relates to a receptacle, for use with an apparatus for generating an inhalable medium, a cartridge for use with an apparatus for generating an inhalable medium, an apparatus for generating an inhalable medium and a method of generating an inhalable medium.

BACKGROUND

Smoking articles such as cigarettes, cigars and the like burn tobacco during use to create tobacco smoke. Attempts have been made to provide alternatives to these articles that burn tobacco by creating products that release compounds without burning. Examples of such products are heating devices which release compounds by heating, but not burning, the material. The material may be for example tobacco or other non-tobacco products, which may or may not contain nicotine. As another example, there are so-called e-cigarette devices. These devices typically contain a liquid which is heated to vaporize the liquid to produce an inhalable vapor or aerosol. The liquid may contain nicotine and/or flavorings and/or aerosol-generating substances, such as glycerol. The known e-cigarette devices typically do not contain or use tobacco.

SUMMARY

In one example, there is provided a receptacle for use with an apparatus for generating an inhalable medium, the receptacle comprising: a chamber for containing a flavor material, whereby, in use, at least one of a vapor and an aerosol generated by the apparatus can flow through the flavor material to entrain one or more constituents from the flavor material to produce the inhalable medium; and wherein the receptacle is configured to maintain an air gap separation between an outlet end of the chamber and flavor material when it is received in the chamber, the outlet end being configured to enable the inhalable medium to flow out of the chamber.

The provision of the air gap separation significantly reduces excessively large liquid droplets formed by condensation escaping from the flavor material and reaching the consumer's mouth, which significantly improves the sensory experience of the consumer.

According to a second example, there is provided a cartridge for use with an apparatus for generating an inhalable medium, the cartridge comprising a receptacle for use with an apparatus for generating an inhalable medium, the receptacle comprising: a chamber for containing a flavor material, whereby, in use, at least one of a vapor and an aerosol generated by the apparatus can flow through the flavor material to entrain one or more constituents from the flavor material to produce the inhalable medium; and wherein the receptacle is configured to maintain an air gap separation between an outlet end of the chamber and flavor material when it is received in the chamber, the outlet end being configured to enable the inhalable medium to flow out of the chamber, the cartridge also includes a container for holding a liquid, the arrangement being such that in use liquid exiting the container can flow, in the form of at least one of a vapor and an aerosol, through flavor material received in the receptacle to thereby entrain one or more constituents from the flavor material to produce the inhalable medium which passes out of the outlet end of the chamber via the separation between the air gap separation between the outlet end of the chamber and flavor material received in the chamber.

According to a third example, there is provided an apparatus for generating an inhalable medium, the apparatus comprising as described in the second example above; and a battery section.

According to a fourth example, there is provided a method of generating an inhalable medium using the apparatus for generating an inhalable medium, the method comprising: heating liquid drawn from the container to vaporize the liquid; passing the vaporized liquid through the receptacle containing the flavor material and through the flavor material so as to entrain at least flavor from the flavor material; and passing the flavored aerosol through the air gap separation between the outlet end of the chamber and the flavor material received in the chamber.

BRIEF DESCRIPTION OF THE DRAWINGS

Embodiments of the disclosure will now be described, by way of example only, with reference to the accompanying drawings, in which:

FIGS. 3a to 3f show schematic longitudinal cross-sectional views of an example of a cartridge having a liquid container and a receptacle for solid material and components thereof.

FIGS. 4a to 4e show schematic longitudinal cross-sectional views of an example of a cartridge having a liquid container and a separate receptacle for solid material and components thereof.

FIGS. 5a to 5e show schematic longitudinal cross-sectional views of an example of a cartridge having a liquid container and a separate receptacle for solid material and components thereof.

DETAILED DESCRIPTION

Figure 1:
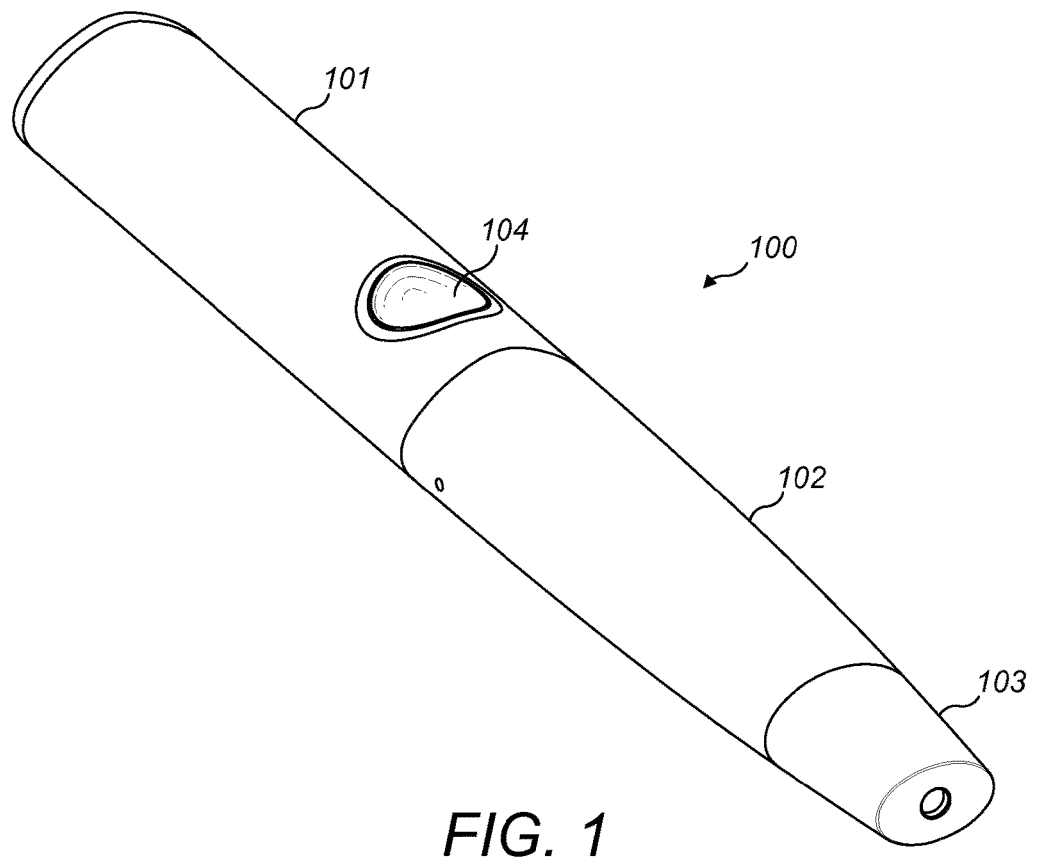
FIGS. 1 and 2 show respectively a perspective view and a side elevation of an example of an apparatus for generating an inhalable medium.

Referring to FIG. 1, there is shown an example of an apparatus 100 for generating an inhalable medium. In broad outline, the apparatus 100 volatilizes a liquid to form a vapor or an aerosol which passes through a material so as to produce an inhalable medium that contains one or more constituents derived from the material.

In this respect, first it may be noted that, in general, a vapor is a substance in the gas phase at a temperature lower than its critical temperature, which means that for example the vapor can be condensed to a liquid by increasing its pressure without reducing the temperature. On the other hand, in general, an aerosol is a colloid of fine solid particles or liquid droplets, in air or another gas. A "colloid" is a substance in which microscopically dispersed insoluble particles are suspended throughout another substance.

Figure 2:
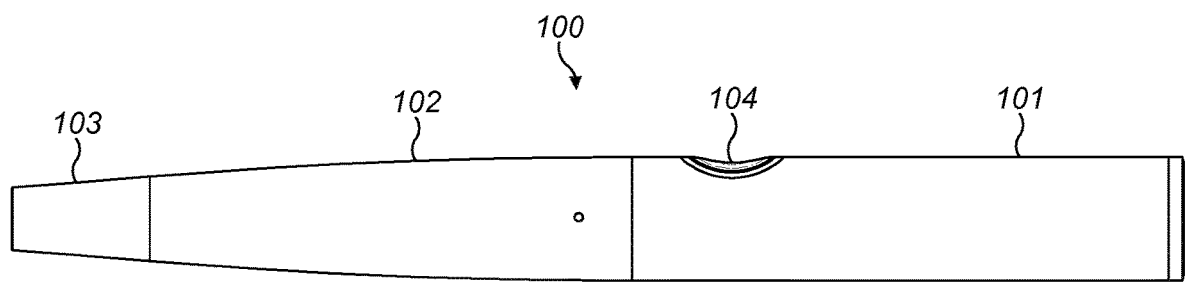

FIGS. 1 and 2 show respectively a perspective view and a side elevation of the example of an apparatus 100 for generating an inhalable medium. The apparatus 100 may be used with any of the cartridges and receptacles described herein and with other cartridges and receptacles. The apparatus 100 has a battery section 101 and a cartridge section 102. The battery section 101 and the cartridge section 102 are shown connected to each other in the drawings, but can be separated by a user to allow a cartridge to be loaded into the cartridge section 102. The battery section 101 and the cartridge section 102 can be separably connected to each other using for example a snap-fit connection, clips, a screw thread, etc. The cartridge section 102 has a mouthpiece 103 at its proximal end. In this example, the battery section 101 has an on-off or power button 104. The battery section 101 contains a power supply (not shown In FIGS. 1 and 2), such as a battery which may be a rechargeable battery or a disposable battery. The battery section 101 also contains a controller (not shown In FIGS. 1 and 2) for controlling the operation of various components of the apparatus 100 and/or a puff detector. In use, the cartridge may be replaceable. The user can operate the apparatus 100 using the on-off or power button 104.

Figure 3F:
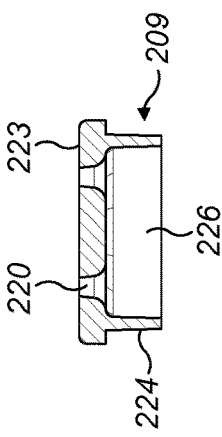
Figure 3E:
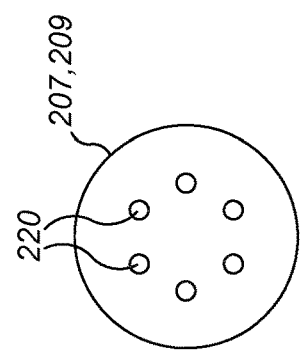
Figure 3D:
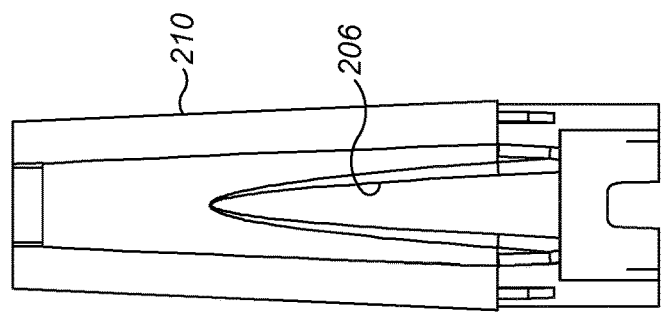

Referring now to FIGS. 3a to 3f, there is shown an example of a cartridge 200 having a liquid container 201 for containing liquid 202 and a receptacle or container 203 for flavor material 204, which will typically be solid material 204. In this example, the liquid container 201 and the material container 203 are provided as one integral component by being formed initially of two parts, shown separately in FIGS. 3b and 3c, which are then assembled as shown in FIG. 3a in a substantially permanent fashion. The liquid container 201 and the material container 203 may be fixed to each other by for example friction welding, such as spin welding, ultrasonic welding, or molded as a single piece etc. The cartridge 200 is arranged so that as the liquid 202 is volatilized so as to produce an aerosol of liquid droplets or sufficiently heated to produce a vapor, at least some and in some embodiments all or substantially all of the aerosol or vapor passes through the material 204 to pick up flavor and/or other volatiles from the material 204.

The liquid container 201 of the cartridge 200 has an outer shell 205 around the outside of the length of the inner liquid container part 210. A channel 206 extends from one end of the liquid container 201 to the other. In the example shown, this channel is provided by a groove 206 in the outer wall of the inner liquid container part 210, as can be seen most clearly in FIG. 3d. The cartridge 200 has a heater 211 for heating liquid and a wick 212 in thermal contact with the heater 211. The heater 211 may be for example an electrically resistive heater, a ceramic heater, etc. In this example, the heater 211 and the wick 212 are provided as a single unit. In this case, where the cartridge 200 includes a heater 211, such a cartridge is often referred to as a "cartomizer."

In the example shown in FIGS. 3a and 3b, the heater 211, which may be, for example, a coil, has its longitudinal axis perpendicular to that of the cartridge 200. Other orientations of the heater 211 are possible, for example, it may be arranged with its longitudinal axis parallel to that of the cartridge 200.

The receptacle 203 for the solid material 204 includes a chamber 208 for receiving flavor material 204 and an end cap 209 for capping an outlet of the chamber 208. The receptacle 203 has one or more walls, which surround the chamber 208. The walls of the receptacle 203 are configured to engage with the container 201 for holding liquid 202 to hold the receptacle 203 in place. In one example, the walls are shaped to engage in a snap fit with the container 201 for holding liquid 202, such that no further attachment means are required to connect the receptacle 203 to the container 201. The receptacle 203 is closed off at the mouth end by the end cap 209, which is spaced from an end wall 207 of the liquid container 201.

The wick 212 is in contact with the liquid 202. As above, this may be achieved by for example the wick 212 being inserted through a through hole in a second end wall 213 of the inner liquid container part 210. Alternatively or additionally, the second end wall 213 may be a porous member which allows liquid to pass through from the inner liquid container part 210, and the wick 212 may be in contact with the porous second end wall 213. The second end wall 213 may be for example in the form of a porous and permeable ceramic disk. The wick 212 is generally absorbent and acts to draw in liquid 202 from the inner liquid container part 210 by capillary action. The wick 212 can be non-woven and may be for example a cotton or wool material or the like, or a synthetic material, including for example polyester, nylon, viscose, or the like, or a ceramic material.

In use, the cartridge 200 is connected by the user to a battery section of an apparatus (which may for example be an apparatus 100 like that shown in FIGS. 1 and 2) to enable the liquid heater 211 to be powered. When the liquid heater 211 is powered (which may be instigated for example by the user operating the button 104 of the overall apparatus 100 or by a puff detector of the overall apparatus 100, as is known per se), liquid 202 drawn in from the inner liquid container part 210 by the wick 212 is heated by the heater 211 to volatilize or vaporize the liquid. As the user draws on a mouthpiece 103 of the overall apparatus 100, the vapor or aerosol passes into the channel 206 of the liquid container 201 and into the chamber 208 of the receptacle 203 that contains the solid material 204. The vapor or aerosol picks up flavor and/or other volatiles from the material 204. In the case that the material 204 contains or includes nicotine, the vapor or aerosol may also contain nicotine entrained from the material 204. The vapor or aerosol can then exit the receptacle 203 as shown by the arrow A. A one way valve (not shown) may be provided so that the vapor or aerosol can only exit the cartridge 200 and cannot back-flow to the heater 211 or the electronics of the apparatus as a whole.

In one example, as shown in FIG. 3f, the end cap 209 includes a first section 223 that is configured to extend across the outlet end of the chamber 208 and at least one second section 224 that extends away from the first section 223 into the chamber 208. The first section defines one or more holes or apertures 220 to allow an inhalable medium to flow out of the end cap 209.

In one example, the first section 223 is in the shape of a disk with the one or more through holes 220 across the width of the disk. In one example, the second sections 224 are spaced from a perimeter of the first section 223 to form a lip at the periphery of the end cap 209. The second sections 224 of the end cap 209 are configured to fit within the chamber 208 such that the second sections 224 fit within the walls of the receptacle 203 for the solid material and extend along the longitudinal axis of the chamber 208. In one example, the second sections are flush with walls 225 of the chamber 208.

The first section 223 of the end cap 203 has an inner face, which faces into the chamber 208 and an outer face, which faces away from the chamber 208. The one or more second sections 224 project from the inner face of the first section 223 into the chamber 208.

In one example, the first section or disk 223 has a diameter of between 7 mm and 9 mm, for example 8.2 mm. In one example, the disk 223 has a thickness of between 0.5 mm and 1.5 mm, for example 1 mm.

The receptacle 203 is configured to maintain an air gap separation 226 between the outlet end of the chamber 208 and flavor material 204 received in the chamber 208.

In one example, the separation 226 is provided by the one or more second sections 224 of the end cap 203, which project from the first section of the end cap 203 into the chamber 208. In this example, the flavor material 204 is maintained at a distance away from the inner face of the first section 223 of the end cap 203 by the one or more second sections 224. This separation 226 provides for an air gap between the edge of the flavor material 204 and the outlet of the receptacle 203.

In another example, the separation 226 is provided by a ridge (not shown) provided on an inner surface of the wall of the receptacle 203, which projects into the chamber 208.

The second section 224 may comprise a single side wall, which projects from an inner face of the end cap 209, which in one example is a continuous, annular wall. In another example, the second section 224 comprises one or more members that extend from the inner face of the first section 223 into the chamber 208. The one or more members may comprise a single cylindrical member or a plurality of members that extend from the inner face of the first section 223, the plurality of members being made of arcuate elements which are arranged in an annular relationship on the inner face.

The second section 224 prevents the flavor material 204 from contacting the inner face of the end cap 209 as the second section 224 of the end cap 209 is arranged to abut the flavor material 204 received in the receptacle 203.

Partial condensates may form on the solid flavor material 204 that cause saturation of the vapor or aerosol, which may result in excessively large liquid droplets forming and escaping from the solid flavor material 204. Such liquid droplets formed by condensation can become entrained in the airflow as large, non-inhalable droplets and negatively affect the sensory experience of a consumer.

The separation 226 provided by the receptacle 203 allows an air gap to exist between the outlet of the receptacle 203 and the solid flavor material 204. The air gap between the solid flavor material 204 and the outlet of the receptacle 203 significantly reduces excessively large liquid droplets formed by condensation escaping from the consumable and reaching the consumer's mouth, which significantly improves the sensory experience of the consumer.

In one example, the end cap 209 includes a single hole 220. In other example, the end cap 209 includes a plurality of holes 220 arranged in an annular relationship. In another example, the end cap comprises six holes 220 (see FIG. 3e).

Figure 3C:
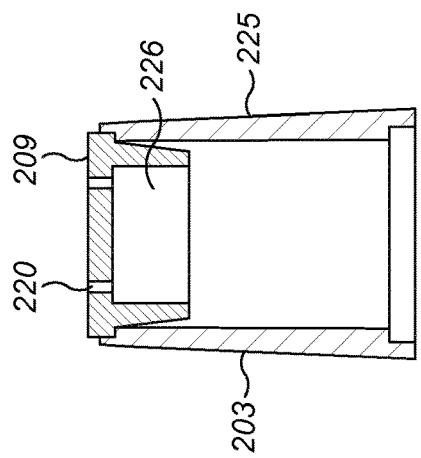

The end cap 209 of the chamber 208 may be provided by a separate retainer 209, as in the examples shown in FIGS. 3a, 3c and 3f, which is inserted into the chamber 208 during manufacture. As an alternative, the end cap 209 may be an integral part of the receptacle 203. The end cap 209 may be formed of plastics or rubber or ceramic or the like.

In the example shown in FIG. 3a and FIG. 3b, the end wall 207 of the liquid container 201 is an integral part of the liquid container 201, for example by molding the end wall 207 with the liquid container 201. In other examples, the end wall 207 of the liquid container 201 may be provided by a separate retainer, for example in the form of a disk which is fitted to the liquid container 201 during manufacture. The end wall 207 may be formed of plastics or rubber or ceramic or the like and has one or more through holes 220 to allow aerosol or vapor to pass into the chamber 208 which contains the solid material 204.

The end wall 207 of the liquid container 201 and the end cap 209 of the solid material chamber 208 assist in retaining the solid material 204 in position in the solid material chamber 208, both during transport of the cartridge 200 and during use of the cartridge 200.

One or more projections 227 may project from the end wall 207 into the receptacle 203, when the receptacle is 203 is attached to the liquid container 201. The one or more projections 227 may be annular in shape. In one example, the walls 225 of the chamber 208 are shaped to engage with the one or more projections 227 such that there is a snap fit between the receptacle 203 and the liquid container 201. An element 228 may be provided across the top of the projections 227 to provide a separation 229 between the end wall 207 and the flavor material 204 held within the receptacle 203.

In other examples, the end wall 207 may be flush with the solid material 204, whereas the first section 223 of the end cap 209 will be separated from the flavor material due to the presence of second section 224, which projects into the flavor material to form an air gap separation 226.

In one example, the at least one second section 224 has a length of between 1 mm and 5 mm, for example 2 mm, therefore the air gap separation 226 between the outlet end of the chamber and flavor material received in the chamber is between 1 mm and 5 mm, for example 2 mm.

Referring now to FIGS. 4a to 4e, there is shown a further example of a cartridge 300 having a liquid container 301 for containing liquid 302 and a receptacle or container 303 for material 304, which will typically be solid flavor material 304. Many aspects and features of the example of FIGS. 4a to 4e are similar to the example described above with reference to of FIGS. 3a to 3e and a detailed description of those aspects and features will not be repeated here for the sake of brevity.

In this example, the liquid container 301 and the material container 303 are provided as separate parts, shown separately in FIGS. 4c and 4d. The liquid container 301 and the material container 303 may be connected or fixed to each other during manufacture, by for example clipping them together, by friction welding, such as spin welding, ultrasonic welding, etc. As an alternative, the liquid container 301 and the material container 303 may be connected or fixed to each other by the user during use, with the material container 303 being in the form of a removable receptacle. In such a case, the user can easily replace one or other of the liquid container 301 and the material container 303 as required as the liquid 302 and/or solid material 304 is consumed during use. The material container 303 may be fitted to the liquid container 303 by, for example, clips and/or as a friction fit. The cartridge 300 is again arranged so that as the liquid 302 is volatilized so as to produce an aerosol of liquid droplets or sufficiently heated to produce a vapor, at least some and in some embodiments all or substantially all of the aerosol or vapor passes through the material 304 to pick up flavor and/or other volatiles from the material 304.

As described above in relation to FIG. 3, the receptacle 303 for the solid material 304 includes a chamber 308 for receiving a flavor material 304 formed by one or more walls and an end cap 309.

A first section 323 of the end cap 303 has an inner face, which faces into the chamber 308 and an outer face, which faces away from the chamber 308. One or more second sections 324 project from the inner face of the first section 323 into the chamber 308. The receptacle 303 is configured to maintain an air gap separation 326 between the outlet end of the chamber 308 and flavor material 304 received in the chamber 308.

In one example, the separation 326 is provided by the one or more second sections 324 of the end cap 309, which project from the first section of the end cap 309 into the chamber 308. In this example, the flavor material 304 is maintained at a distance away from the inner face of the first section 323 of the end cap 309 by the one or more second sections 324. This separation 326 provides an airgap between the edge of the flavor material 304 and the outlet of the receptacle 303.

In another example, the separation 326 is provided by a ridge (not shown) provided on an inner surface of the wall of the receptacle 303, which projects into the chamber 308.

The second section 324 may comprise a single side wall, which projects from the inner face of the end cap 309, which in one example is a continuous, annular wall. In another example, the second section 324 comprises one or more members that extend from the inner face of the first section 323 into the chamber 308. The one or more members may comprise a single cylindrical member or a plurality of members that extend from the inner face of the first section 323, the plurality of members being made of arcuate elements which are arranged in an annular relationship on the inner face.

The one or more members may comprise a single cylindrical member or a plurality of members that extend from the inner face of the first section, the plurality of members being arranged in an annular relationship on the inner face.

The second section 324 prevents the flavor material 304 from contacting the inner face of the end cap 309 as the second section 324 of the end cap 309 is arranged to abut the flavor material 304 received in the receptacle 303.

Partial condensates may form on the solid material 304 that cause saturation of the flavor material, which may result in liquid droplets forming and escaping from the solid material 304. Such liquid droplets will negatively affect the sensory experience of a consumer due to the effect on taste and make-up of the vapor or aerosol exiting the solid material 304.

The separation 326 provided by the receptacle 303 allows an air gap to exist between the outlet of the receptacle 303 and the solid material 304. The air gap between the solid material 304 and the outlet of the receptacle 303 significantly reduces excessively large liquid droplets formed by condensation escaping from the consumable and reaching the consumer's mouth, which significantly improves the sensory experience of the consumer.

The first section 323 of the end cap 309 has one or more through holes 320 to allow aerosol or vapor to pass through the mouth end of the receptacle 303. In one example, the end cap 309 includes a single hole 320. In other example, the end cap 309 includes a plurality of holes 320 arranged in an annular relationship. In another example, the end cap comprises six holes 320.

The receptacle 303 for the solid material 304 is closed off at the mouth end by the end cap 309. In the example shown in FIGS. 4a to 4c, the end cap 309 at the mouth end of the chamber 308 comprises a disk portion 323 and one or more legs 324 that project from a surface of the disk portion 323 of the end cap 309 into the chamber 308.

The end cap 309 may be inserted into the chamber 308 during manufacture. The end cap 309 may be formed of plastics or rubber or ceramic or the like and has one or more through holes 320 through the first section 323 to allow aerosol or vapor to pass through the mouth end of the cartridge 300. As an alternative, the end cap 309 may be an integral part of the receptacle 303, and similarly has one or more through holes to allow aerosol or vapor to pass through the mouth end of the cartridge 300 to be inhaled by a user.

In one example, the at least one second section 324 has a length of between 1 mm and 5 mm, for example 2 mm therefore the air gap separation 326 between the outlet end of the chamber and flavor material received in the chamber is between 1 mm and 5 mm, for example 2 mm.

In a further alternative, the chamber 308 may have a second end wall (not shown) having through holes, spaced from the end wall or disk 309 at the mouth end. In this way, the chamber 308 for the solid material 304 can provide a complete unit that contains the solid material 304, which facilitates manufacture of the overall cartridge 300 and/or simplifies replacement of the chamber 308 by the user once the solid material 304 has been consumed.

Similarly, in the example shown in FIGS. 4a to 4e, a disk 307 may be provided which is fitted to the liquid container 301 during manufacture to act as an end wall of the liquid container 301. The disk 307 may be formed of plastics or rubber or ceramic or the like and has one or more through holes 320 to allow aerosol or vapor to pass into the chamber 308 which contains the solid material 304. As an alternative, the end wall 307 may be an integral part of the liquid container 301, and similarly has one or more through holes to allow aerosol or vapor to pass through.

In the example of FIGS. 4a to 4e, the receptacle or container 303 has a female connector. A portion of the wall 325 of the receptacle 303 fits over the end of the liquid container 301 in use.

In FIGS. 5a to 5e, there is shown another example cartridge 400 having a liquid container 401 for containing liquid 402 and a receptacle or container 403 for flavor material 404, which will typically be solid material 404. The example of FIGS. 5a to 5e is very similar to the example of FIGS. 4a to 4e except that in this case, the material container 403 has a male connector, in which a portion of the wall of the material container 403 is an annular end wall 421 which fits within the end of the liquid container 401 in use. FIGS. 5a to 5e also show an example of the embodiment mentioned above in which the material container 403 has a second end wall $409^1$ having through holes, spaced from the end wall or disk 409 at the mouth end, so that the chamber 408 for the solid material 404 provides a complete unit that contains the solid flavor material 404.

In FIGS. 6a to 6e, there is shown examples of end caps that may be used in at least some of the examples described above.

Figure 6A:
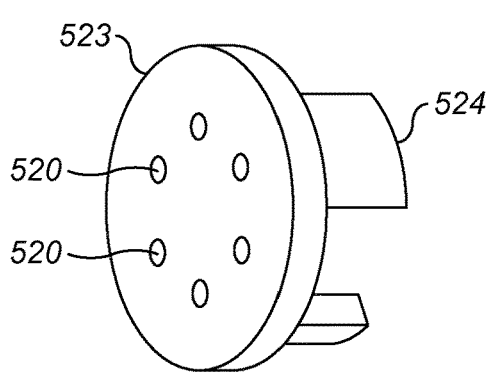
FIGS. 6a to 6e show schematic perspective views of different end caps.

FIG. 6a shows an end cap comprising a first section 523 and a plurality of members 524 projecting from an inner face of the disk portion 523. The members 524 are formed of arcuate elements and are arranged in an annular fashion. The members 524 may be of uniform or alternatively may be wider on one side than the other.

Figure 6B:
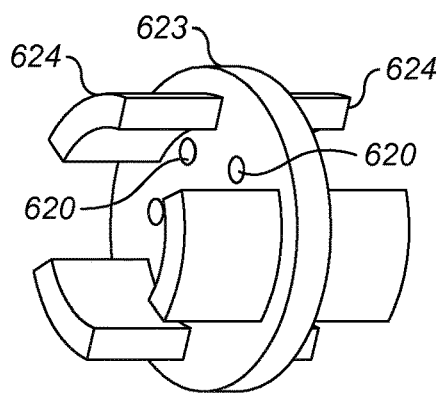
Figure 6C:
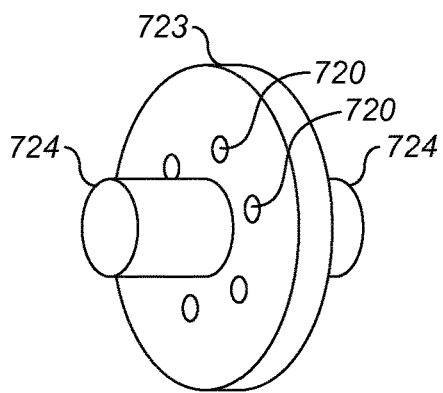

FIGS. 6b and 6c both show an end cap comprising a first section 623, 723 formed of a disk portion and at least one second section 624, 724 projecting from the inner face of the first section. In the example shown in FIGS. 6b and 6c there are one or more projections 624, 724 projecting from the outer face of the first section in addition to the projections 624, 724 projecting from the inner face of the first section. Providing projections on both sides of the first section can make manufacture and assembly more straightforward and enables the end cap to be attached either way up to a receptacle. The projections may be 624, 724 may be uniform or alternatively may be wider on one side that the other.

FIG. 6b shows a plurality of arcuate shaped members projecting in an annular fashion from each side of the section 623, whilst FIG. 6c shows a cylindrical member projecting from each side of the section 723.

Figure 6D:
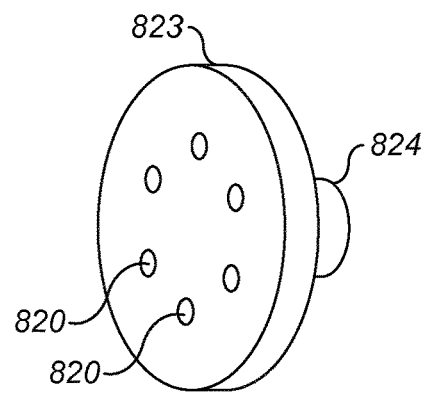

FIG. 6d shows an example of an end cap comprising a first section 823 formed of a disk and a single member projecting from one face of the disk 823. The member is cylindrical and projects from an inner face of the disk 823.

Figure 6E:
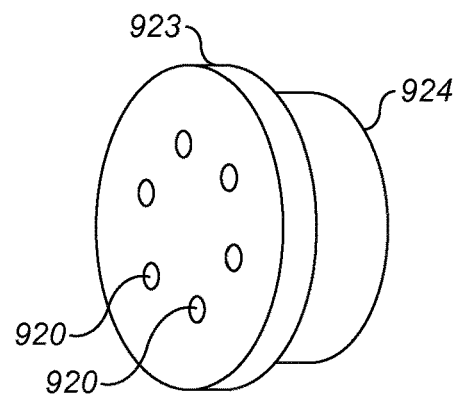

FIG. 6e shows an end cap comprising a first section 923 and a single annular member 924 projecting from an inner face of the disk portion 923.

The examples shown in FIGS. 3 to 5 are suitable for use with so-called modular products, in which the cartomizer is fitted to a battery section of an overall apparatus (such as a battery section 101 of an apparatus 100 as shown in FIGS. 1 and 2), typically by a screw thread, a bayonet fitting or the like. The cartomizer as a whole is typically discarded after use and a new, replacement cartomizer used. As an alternative, it may be possible for the user to re-use the cartridge by refilling the liquid and/or replacing the solid material from time to time as necessary.

The examples shown in FIGS. 3 to 5 may easily be adapted for use with other types of e-cigarette apparatus, which are known per se. There are for example so-called "look alike e-cigarette" or "cig-alike" devices which are generally small and have a form and appearance similar to a conventional cigarette. In such devices, the liquid container typically includes some wadding material, of for example cotton or the like, for holding the liquid. The cartridge or cartomizer in such known devices is typically disposable as a whole, but it may be possible to refill the liquid and/or replace the solid material in examples that use an embodiment of the present disclosure. As another example, there are so-called tank devices or personal vaporizers which generally have large liquid containers for holding relatively large volumes of liquid and also provide for advanced functions that allow users to control a number of aspects of the device.

As an alternative to any of the cartomizer arrangements discussed above, the heater for the liquid may be provided separately of the liquid and material containers. The heater may for example be provided as part of the battery section 101 of the overall apparatus 100 to which the cartridge is detachably fitted by the user in use.

In any of the examples described above in relation to FIGS. 3 to 5, there may also be provided a heater for the solid material so as to heat and/or "pre-heat" the solid material. This solid material heater may be provided as part of the cartridge or as part of the battery section of the apparatus to which the cartridge is fitted in use.

A number of other variations and alternatives to the examples described above are possible.

For example, in some cases it may be possible for the solid material to be located, exclusively or additionally, in the mouthpiece of the apparatus (e.g. the mouthpiece 103 of an apparatus 100 as described above) which with the cartridge described above is used.

As another example, the solid material may be omitted from the container, for example at the option of the user. This provides the user with more flexibility over the use of the cartridge as the user can use the cartridge as a classic "e-cigarette" device, only vaporizing liquid and not having the vapor or aerosol pass over or through solid material, from time to time if they choose. This is particularly the case for the examples where the solid material in the solid material container is replaceable by the user.

It is described above that the channel through which aerosol/vapor flows from the liquid heater to the solid material is annular and completely surrounds the liquid container in some examples. This annular section may be uniform or wider on one side than the other. In other examples, the channel is not annular and does not surround the liquid container, etc. As another example, there may be plural channels or grooves extending from the liquid container to the solid material, one or more of which may be substantially tubular. Where there are plural channels, it is possible for the channels to be filled with or contain or lead to materials having different properties. For example, one channel may be filled with or contain or lead to a material that imparts a first flavor to the vapor or aerosol, a second channel may be filled with or lead to a material that imparts a second flavor to the vapor or aerosol, etc.

In the examples above, the liquid container and the solid material/solid material container are arranged substantially in-line, along a longitudinal axis of the apparatus or cartridge. In other examples, the liquid container and the solid material/solid material container are arranged so as to at least partially overlap in the longitudinal direction of the apparatus or cartridge; in such examples, the liquid container and the solid material/solid material container may still be arranged generally in-line along the longitudinal axis of the apparatus or cartridge, or may be arranged side by side, or with one partially or completely inside the other. In yet other examples, the liquid container and the solid material/solid material container are arranged concentrically (either with the liquid container inside the solid material/solid material container or vice versa), and may be arranged to be entirely off-set with respect to each other along the longitudinal axis of the apparatus or cartridge, or overlapping, or one completely within the other.

As another specific example, the solid material/solid material container is placed in at least one channel between the heater and the outlet, the channel at least partially overlapping with the liquid container in the longitudinal axis of the apparatus or cartridge. In other words, the vapor or aerosol flow channel goes past the liquid container and the material is located somewhere within the channel.

The cartridge may comprise a cooler or heat exchanger, and/or the apparatus with which the cartridge 200, etc., is used may comprise a cooler or heat exchanger. The material and the cooler in such an arrangement may be separate and spaced from each other. The cooler may be downstream of the liquid heater and upstream of the receptacle, the cooler or cooling zone being arranged to cool vaporized liquid to form an aerosol of liquid droplets which in use passes through material received in the receptacle. The cooler may be arranged in effect to act as a heat exchanger, allowing for recovery of heat from the vapor. The recovered heat can be used for example to pre-heat the material and/or to assist in heating the liquid.

As described in relation to the examples above, the liquid can be a liquid that is volatilizable at reasonable temperatures, for example in the range of 100-300° C. or more particularly around 150-250° C., as that helps to keep down the power consumption of the apparatus with which the cartridge is used. Suitable materials include those conventionally used in e-cigarette devices, including for example propylene glycol and glycerol (also known as glycerine). In one example, the liquid includes tobacco extract. Also as described in relation to the examples above, the solid material is a material that may be used to impart a flavor to the aerosol or vapor produced from the liquid as the aerosol or vapor passes through the material. The material may for example consist of or comprise tobacco. As the aerosol or vapor passes through and over the tobacco material, the hot aerosol or vapor entrains organic and other compounds or constituents from the tobacco material that lend tobacco its organoleptic properties, thus imparting the flavor to the aerosol or vapor as it passes to the mouthpiece. It will be understood however that materials other than tobacco may be used to impart different flavors to the aerosol or vapor stream. For example, flavorants could be included in the material or in the liquid.

In any of the examples described above, the apparatus controller controls operation of the apparatus as a whole. The controller for example may cause liquid heater and/or the solid material heater to be powered as and when required and switch off the liquid heater and/or the solid material heater when heating is not required. Operation of the one or more heaters may be controlled so that the liquid and/or material is heated to an optimum temperature. Particular considerations include ensuring that the material does not burn, ensuring that adequate vaporization of the liquid is achieved, ensuring that the vaporized liquid or aerosol is at an appropriate temperature to liberate compounds from the material, and ensuring that the vapor or aerosol that reaches the user is at a comfortable and safe temperature. A puff detector, a device which is known per se, may be provided to signal to the controller when the one or more heating elements need to be energized. The apparatus may also have one or more filters for filtering the vapor or aerosol before it reaches the user, cooling arrangements for cooling the vapor or aerosol before it reaches the user, insulation internally of the apparatus to protect the user from the heat generated inside the housing, etc.

As described in more detail above, the material may be heated only by the hot vapor or aerosol that passes through the material. Alternatively, the material may also be pre-heated or dual-heated using for example a dedicated heater. In the case of pre-heating, the material, particularly in the case of tobacco, may be pre-heated to a temperature in the range of around 100 to 150° C. It will be appreciated however that other temperatures may be used. The amount of tobacco present may be for example in the range 50 to 300 mg or so. A most suitable value for the amount of tobacco may be for example in the range 50 to 150 mg, with 110 mg being a value that is currently found to be particularly suitable in some applications. Suitable materials 104, 204 etc. include materials that provide volatilized components upon heating, typically in the form of an aerosol or vapor. Suitable materials 104, 204 etc., include any tobacco-containing material and may, for example, include one or more of tobacco per se, different varieties of tobacco, tobacco derivatives, expanded tobacco, reconstituted tobacco, ground tobacco, tobacco extract, homogenized tobacco or tobacco substitutes. In the case of tobacco, the material 104, 204 etc. may be in the form of a rod of tobacco, a pod or plug of tobacco, loose tobacco, agglomerates, etc., and may be in relatively dry form or in relatively moist form, for example. Suitable materials 104, 204 etc. may include other, non-tobacco, products, which, depending on the product, may or may not contain nicotine.

In the particular case that the solid material is tobacco, the tobacco may be in the form of a plug of tobacco rod which is cut to length and placed into the receptacle or container for the solid material before the receptacle or container for the solid material is combined with the liquid container (whether the receptacle or container for the solid material is combined with the liquid container during manufacture or by the user in use).

In some examples, the receptacle or container for the solid material is transparent, so that the user can see the contents (i.e. the solid material) in use, which is appealing to some users. The tobacco rod may be formed using a transparent material as a wrapping material, again so that the user can see the tobacco. A particularly suitable material is "Nature-Flex" (trade mark), a biodegradable film made from renewable raw materials by Innovia Films Limited.

As used herein, the terms "flavor" and "flavorant" refer to materials which, where local regulations permit, may be used to create a desired taste or aroma in a product for adult consumers. They may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, or powder.

In order to address various issues and advance the art, the entirety of this disclosure shows by way of illustration and example various embodiments in which the claimed invention may be practiced and which provide for a superior apparatus arranged to generate an inhalable medium. The advantages and features of the disclosure are of a representative sample of embodiments only, and are not exhaustive and/or exclusive. They are presented only to assist in understanding and teach the claimed and otherwise disclosed features. It is to be understood that advantages, embodiments, examples, functions, features, structures and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist in essence of, various combinations of the disclosed elements, components, features, parts, steps, means, etc. The disclosure may include other inventions not presently claimed, but which may be claimed in future.

The invention claimed is:

1. A receptacle for use with an apparatus for generating an inhalable medium, the receptacle comprising:
    a chamber for containing a flavor material, the chamber being configured to cause at least one of a vapor or an aerosol generated by the apparatus to flow through the flavor material to entrain one or more constituents from the flavor material to produce the inhalable medium, in use; and
    an end cap for capping an outlet end of the chamber, the end cap defining at least one hole configured to enable the inhalable medium to flow out of the outlet end of the chamber;

wherein the receptacle is configured to maintain an air gap separation between the outlet end of the chamber and the flavor material when the flavor material is received in the chamber;

wherein the end cap comprises a first section that extends across the outlet end of the chamber and which defines the at least one hole, and the receptacle further comprises at least one second section that extends away from the first section into the chamber to maintain the air gap separation; and wherein the receptacle is a mouthpiece or a part of a mouthpiece for the apparatus for generating an inhalable medium.

2. The receptacle according to claim 1, wherein the at least one second section comprises a side wall of the end cap.

3. The receptacle according to claim 1, wherein the at least one second section comprises one or more members that extend from an inner face of the first section.

4. The receptacle according to claim 3, wherein the one or more members comprises a single cylindrical member.

5. The receptacle according to claim 3, wherein the one or more members comprises a plurality of members that extend from the inner face of the first section, the plurality of members being arranged in an annular relationship on the inner face.

6. The receptacle according to claim 2, wherein the at least one second section is arranged to abut the flavor material received in the receptacle.

7. The receptacle according to claim 1, wherein the end cap comprises a single hole.

8. The receptacle according to claim 1, wherein the end cap comprises a plurality of holes arranged in an annular relationship.

9. The receptacle according to claim 1, wherein the end cap comprises at least six holes.

10. The receptacle according to claim 1, wherein the first section comprises a disk defining the at least one hole.

11. The receptacle according to claim 10, wherein the disk has a diameter of between 7 millimeters (mm) and 9 mm.

12. The receptacle according to claim 10, wherein the disk has a thickness of between 0.5 mm and 1.5 mm.

13. The receptacle according to claim 1, wherein the at least one second section is separated from an edge of the first section to form a lip at a location where the at least one second section meets the first section.

14. The receptacle according to claim 1, wherein the at least one second section has a length of between 1 mm and 5 mm.

15. The receptacle according to claim 1, wherein the air gap separation between the outlet end of the chamber and the flavor material received in the chamber is between 1 mm and 5 mm.

16. The receptacle according to claim 1, wherein the chamber and the end cap are provided as separate components which are detachably connected to each other.

17. The receptacle according to claim 1, wherein the end cap is an integral part of the receptacle.

18. The receptacle according to claim 1, wherein the receptacle has at least one retainer for retaining the flavor material within the receptacle in use.

19. The receptacle according to claim 1, wherein the receptacle contains a solid material.

20. The receptacle according to claim 19, wherein the solid material is or comprises tobacco.

21. The receptacle according to claim 1, wherein the air gap has an axial length of between 1 mm and 5 mm.

22. A cartridge for use with an apparatus for generating an inhalable medium, the cartridge comprising:
a receptacle according to claim 1; and
a container for holding a liquid;
an arrangement of the receptacle and the container being such that in use liquid exiting the container can flow, in the form of at least one of a vapor or an aerosol, through the flavor material received in the receptacle to thereby entrain one or more constituents from the flavor material to produce the inhalable medium which passes out of the outlet end of the chamber via the air gap separation between the outlet end of the chamber and the flavor material received in the chamber.

23. The cartridge according to claim 22, further comprising a heater associated with the container for volatilizing the liquid held in the container in use.

24. The cartridge according to claim 22, further comprising a heater associated with the receptacle for heating the material received by the receptacle in use.

25. The cartridge according to claim 22, wherein the container has one or more apertures to allow at least one of a vapor or an aerosol to exit the container.

26. The cartridge according to claim 22, further comprising a wick for wicking the liquid held in the container in use out of the container.

27. The cartridge according to claim 22, wherein the container and the receptacle are provided as an integral component.

28. The cartridge according to claim 22, wherein the container and the receptacle are provided as separate components which are detachably connected to each other.

29. The cartridge according to claim 22, wherein the container holds a liquid.

30. An apparatus for generating an inhalable medium, the apparatus comprising:
a cartridge according to claim 22; and
a battery section.

31. A method of generating an inhalable medium using the apparatus of claim 30, the method comprising:
heating liquid drawn from the container to vaporize the liquid;
passing the vaporized liquid through the receptacle containing the flavor material and through the flavor material so as to entrain at least flavor from the flavor material; and
passing the flavored aerosol through the air gap separation between the outlet end of the chamber and the flavor material received in the chamber.

* * * * *